US00PP37087P2

(12) United States Plant Patent
Smith

(10) Patent No.: US PP37,087 P2
(45) Date of Patent: Nov. 4, 2025

(54) ***CHRYSANTHEMUM* PLANT NAMED 'CIFZ0114'**

(50) Latin Name: ***Chrysanthemum* x *morifolium***
Varietal Denomination: CIFZ0114

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,411

(22) Filed: Jan. 23, 2025

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./263.1, 284, 286, 287, 293
See application file for complete search history.

(56) References Cited

U.S. PATENT DOCUMENTS

PP25,143 P2 * 12/2014 Smith ..... A01H 6/1424
Plt./297

* cited by examiner

*Primary Examiner* — Karen M Redden
(74) *Attorney, Agent, or Firm* — Dale Skalla

(57) ABSTRACT

A new garden type *Chrysanthemum* plant named 'CIFZ0114' particularly distinguished by its medium size plant with round plant habit, a medium size duplex to decorative flower with purple flower color, and a natural season response in mid-October.

1 Drawing Sheet

Figure 1:
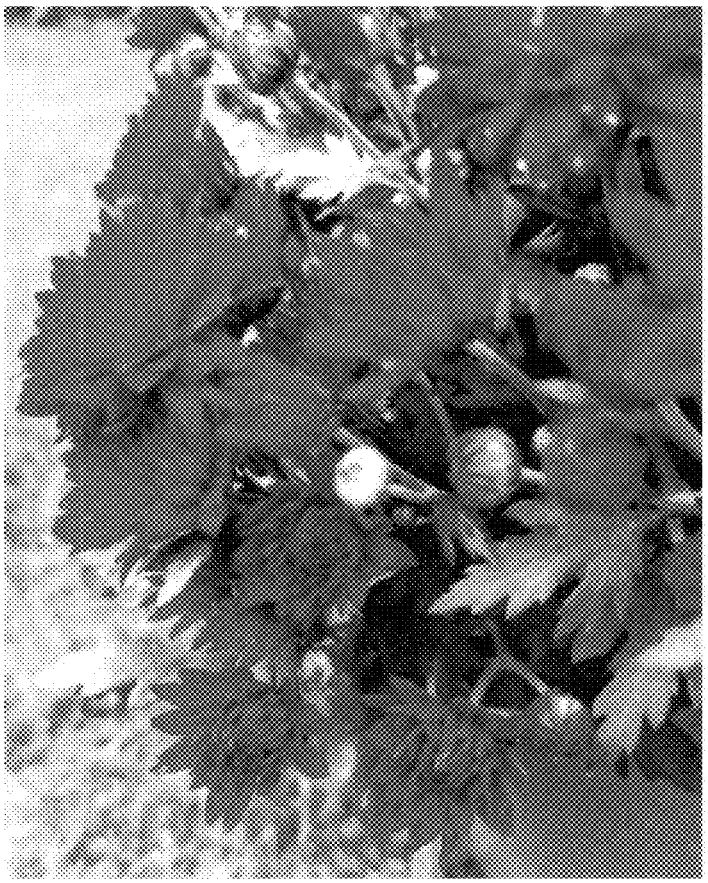

Latin name of the genus and species of the plant claimed: *Chrysanthemum* x *morifolium.*

Varietal denomination: 'CIFZ0114'.

BACKGROUND OF THE NEW PLANT

The present invention comprises a new *Chrysanthemum*, botanically known as *Chrysanthemum* x *morifolium*, and hereinafter referred to by the variety name 'CIFZ0114'.

'CIFZ0114' is a product of a planned breeding program. The new cultivar has medium size plant with round plant habit, a medium size duplex to decorative flower with purple flower color, and a natural season response in mid-October.

'CIFZ0114' originated from a cross made in October 2019 in Enkhuizen, The Netherlands. Seeds were sown in June 2020 in Alva, Florida and 'CIFZ0114' was selected from the resulting population on Nov. 13, 2020 in Alva, Florida.

The female parent was an unnamed proprietary seedling 'FB0015', a purple decorative.

TABLE 1

Characteristics of the female parent, compared to 'CIFZ0114':

| | 'CIFZ0114' | 'FB0015' |
|---|---|---|
| Natural response: | Similar | Similar |
| Flower size: | Smaller | Larger |
| Flower color: | Similar | Similar |
| Flower type: | Less disc florets | More disc florets |
| Plant size: | Smaller | Larger |
| Plant habit: | Similar | Similar |
| Flowering uniformity: | Similar | Similar |

The male parent was an unnamed proprietary seedling 'FB0152', orangy yellow daisy.

TABLE 2

Characteristics of the male parent, compared to 'CIFZ0114':

| | 'CIFZ0114' | 'FB0152' |
|---|---|---|
| Natural response: | 4 weeks slower | 4 weeks faster |
| Flower size: | Larger | Smaller |
| Flower color: | Purple | Orangey Yellow |
| Flower type: | Decorative | Daisy |
| Plant size: | Larger | Smaller |
| Plant habit: | Similar | Similar |
| Flowering uniformity: | Similar | Similar |

The first act of asexual reproduction of 'CIFZ0114' was accomplished when vegetative cuttings were propagated from the initial selection in January 2021 in Alva, Florida

BRIEF SUMMARY OF INVENTION

Horticultural examination of plants grown from cuttings of the plant initiated in January 2021 and continuing thereafter, has demonstrated that the combination of characteristics as herein disclosed for 'CIFZ0114' are firmly fixed and are retained through successive generations of asexual reproduction.

'CIFZ0114' has not been observed under all possible environmental conditions. The phenotype may vary significantly with variations in environment such as temperature, light intensity and day length.

A Plant Breeder's Right for this cultivar has not yet been applied for. 'CIFZ0114' has not been made publicly available prior to the effective filing date of this application, notwithstanding any disclosure that may have been made less than one year prior to the effective filing date of this application by the inventor or another who obtained 'CIFZ0114' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0114' with colors being as true as possible with an illustration of this type.

Figure 2:
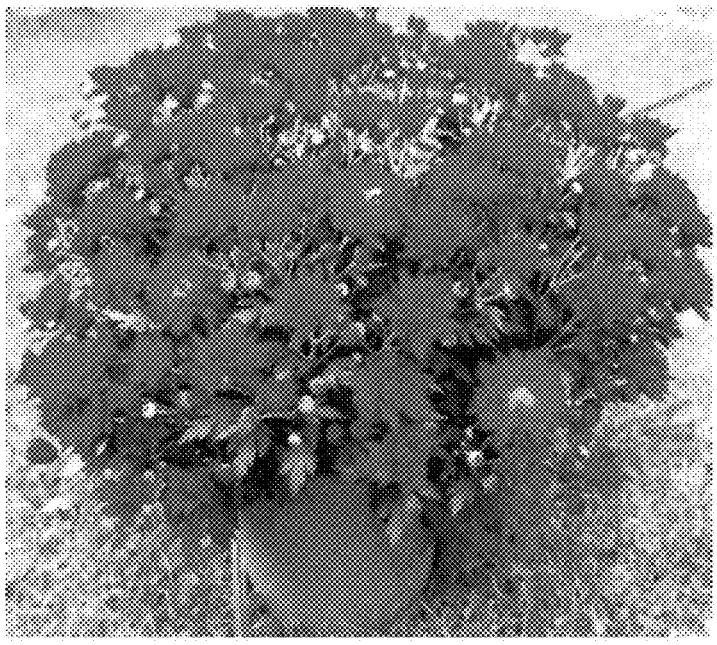

The photographic drawing shows in FIG. 1 a close view of flower of the new variety and in FIG. 2 a flowering plant from an indoor trial.

The aforementioned photographs: FIG. 1, as well as FIG. 2, were taken on Sep. 6, 2024 both showing a plant from the same blackcloth outdoor trial in Andijk, The Netherlands.

These plants were about 13 weeks of age. One rooted cutting per pot had been planted in a 19 cm pot, not pinched in week 23, 2024 and black clothed from week 29. Plants started flowering the end of August 2024.

The measurements were taken in Andijk, The Netherlands in September 2024 on plants from the same outdoor blackcloth trial.

DETAILED BOTANICAL DESCRIPTION

Color references are made to The Royal Horticultural Society Colour Chart (R.H.S.) 2001.

TABLE 3

DIFFERENCES BETWEEN THE NEW VARIETY 'CIFZ0114' AND TWO MOST SIMILAR VARIETIES:

| | 'CIFZ0114' | 'CIFZ0010', U.S. Plant Pat. No. 25,143 |
|---|---|---|
| Natural response: | Not quite 1 week slower | Not quite 1 week faster |
| Blackcloth response: | 0.5 weck slower | 0.5 weck faster |
| Flower size: | Larger | Smaller |
| Flower color: | Similar | Similar |
| Plant size: | Larger | Smaller |
| Plant habit: | Similar | Similar |
| Flower longevity: | More frost tolerant | Less frost tolerant |
| Flowering uniformity: | Less uniform | More uniform |

TABLE 4

| | 'CIFZ0114' | 'Morgana purple', PPAF |
|---|---|---|
| Natural response: | Similar but faster in the heat | Similar but slower in the heat |
| Blackcloth response: | Similar | Similar |
| Flower size: | Similar | Similar |
| Flower color: | Similar | Similar |
| Flower type: | Similar | Similar |
| Plant size: | Larger | Smaller |
| Plant habit: | Similar | Similar |
| Flower longevity: | Less fading | More fading |

Plant:

*Form, growth and habit.*—Herbaceous garden-type, stems Upright and outwardly spreading, freely branching, strong and medium vigorous growth habit.

*Plant height* (*above soil*).—19 cm.

*Plant height* (*inflorescence included*).—23 cm.

*Plant width.*—43 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

Arrangement.—Alternate.

*Immature leaf, color upper surface.*—RHS 137A.

*Immature leaf, color lower surface.*—RHS 137B.

*Mature leaf, color, upper surface.*—RHS 147A.

*Mature leaf, color lower surface.*—RHS 137A.

*Length.*—7.5 cm.

*Width.*—4 cm.

*Shape.*—Ovate, with distinct lobes.

*Base shape.*—Attenuate.

*Apex shape.*—Apiculate.

*Margin.*—3 lobed.

*Number of margin indentations.*—20.

*Depth of margin indentations.*—3-8 mm.

*Leaf length terminal lobe relative to total leaf length.*—1:2.

*Leaf depth lower lateral sinus.*—2.0-2.7 cm.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138B.

*Petiole length.*—1.0 cm.

*Petiole orientation.*—Horizontal.

*Diameter.*—0.2 cm.

*Texture.*—Bifid hairs.

*Presence of stipules.*—Occasionally.

*If present, size of stipules.*—Variable in size; up to 1.0 cm long, 0.2 cm wide.

*Color of stipule.*—RHS 147A.

Stem:

*Quantity of main branches per plant.*—6-7.

*Color of stem.*—RHS 146A.

*Length of stem.*—13-15 cm.

*Diameter.*—0.4 cm.

*Length of internodes.*—0.5-2.0 cm.

*Texture.*—Bifid hairs.

*Color of peduncle.*—RHS 138B.

*Length of peduncle.*—2.0-2.5 cm.

*Peduncle diameter.*—0.2 cm.

*Texture.*—Bifid hairs.

Inflorescence:

*Type.*—Compositae, solitary, duplex to decorative inflorescences borne terminally above foliage, ligulate ray florets arranged in whorls on a capitulum giving a semi-double flower.

*Quantity of short days to flowering* (*response time*).—Approximately 8 weeks.

*Quantity of inflorescences per plant.*—About 340 with some small buds developing.

*Lastingness of individual blooms on the plant.*—About five weeks from first color.

*Fragrance.*—Slightly spicy.

Bud (when showing color):
*Color*.—RHS N78B.
*Length*.—0.8 cm.
*Width*.—0.8 cm.
*Shape*.—Round.
Immature inflorescence (at moment of opening):
*Diameter*.—2.5 cm.
*Color of ray florets, upper surface*.—RHS 61A.
*Color of ray florets, lower surface*.—RHS N79C.
Mature inflorescence:
*Diameter*.—4-5 cm.
*Depth*.—1.5 cm.
*Total diameter of disc*.—1.1 cm.
*Receptacle color*.—RHS 147A.
*Receptacle height*.—0.3 cm.
*Receptacle diameter*.—1.7 cm.
*Length of corolla tube*.—0 cm.
Ray florets:
*Average quantity of florets*.—140.
*Number of whorls per inflorescence*.—9.
*Color of florets, upper surface*.—RHS 71A.
*Color lower surface*.—RHS 70B.
*Length*.—1.7 cm.
*Width/diameter*.—0.4 cm.
*Shape*.—Oblanceolate.
*Apex shape*.—Acute.
*Base shape*.—Moderately concave.
*Margin*.—Entire.
*Margin*.—Type of rolling: Flat.
*Texture, upper surface*.—Papillate.
*Lower surface*.—Papillate.
*Ribs present*.—Yes.
*Number of keels*.—2.
*Profile at widest point*.—Flat.
*Longitudinal axis shape*.—Straight, occasionally weakly reflexing or incurved.
*Longitudinal axis curvature strength*.—Weak.
*Corolla tube shape*.—No tube.
Disc florets:
*Number of disc florets*.—80.
*Width*.—0.1 cm.
*Length*.—0.4 cm.
*Colour*.—Base RHS 145D, top RHS 17A.
Inflorescence (at moment of senescence):
*Color of ray florets, upper surface*.—RHS 71B.
*Color of ray florets, lower surface*.—RHS 72C.
Phyllaries:
*Quantity*.—28.
*Color, upper surface*.—RHS 147B.
*Color, lower surface*.—RHS 137A.
*Length*.—0.4 cm.
*Width*.—0.1 cm.
*Shape*.—Ensiform.
*Apex shape*.—Acute.
*Base*.—Fused.
*Margins*.—Entire.
*Texture, upper surface*.—Glabrous.
*Texture, lower surface*.—Canescent.
Reproductive organs:
*Pistil*.—One.
*Length*.—0.4 cm.
*Style color*.—RHS 2C.
*Style length*.—0.3 cm.
*Stigma color*.—RHS 12B.
*Stigma shape*.—Bi-parted.
*Ovary color*.—RHS 1B.
*Ovary length*.—0.2 cm.
*Ovary width*.—0.1 cm.
Androecium:
*Stamens*.—1, found on only disc florets.
*Color of filaments*.—RHS 157C.
*Length filaments*.—0.2 cm.
*Anther color*.—RHS 12B.
*Anther length*.—0.2 cm.
*Anther shape*.—Oval to club shaped.
*Color of pollen*.—RHS 12A.
*Pollen amount*.—Moderate.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0114' substantially as illustrated and described herein.

* * * * *